(12) United States Patent
Shibasaki et al.

(10) Patent No.: US 6,677,461 B2
(45) Date of Patent: Jan. 13, 2004

(54) LIGANDS AND ASYMMETRIC CATALYSTS MADE BY USING THE SAME

(75) Inventors: Masakatsu Shibasaki, Mitaka (JP); Motomu Kanai, Tokyo (JP); Yoshitaka Hamashima, Sendai (JP)

(73) Assignee: Japan as represented by President of the University of Tokyo, Tokyo (JP)

( * ) Notice: Subject to any disclaimer, the term of this patent is extended or adjusted under 35 U.S.C. 154(b) by 0 days.

(21) Appl. No.: 10/070,724

(22) PCT Filed: Jun. 21, 2001

(86) PCT No.: PCT/JP01/05323
§ 371 (c)(1), (2), (4) Date: Jul. 30, 2002

(87) PCT Pub. No.: WO02/00668
PCT Pub. Date: Jan. 3, 2002

(65) Prior Publication Data
US 2003/0119659 A1 Jun. 26, 2003

(30) Foreign Application Priority Data

Jun. 28, 2000 (JP) .......................................... 2000-194212
Dec. 26, 2000 (JP) .......................................... 2000-395514
Jun. 5, 2001 (JP) .......................................... 2001-169922

(51) Int. Cl.⁷ .......................... C07D 309/10; C07F 9/28
(52) U.S. Cl. ..................................... 549/207; 549/218
(58) Field of Search ................................. 549/207, 218

(56) References Cited

PUBLICATIONS

Hamashima, Y., et al. (2001) Catalytic enantioselective cyanosilylation of ketones: improvement of enantioselectivity and catalyst turn–over by ligand turning. Tetrahedron Letters, 42(4) 691–694.

Hamashima, Y., et al. (2000) Catalytic Enantioselective Cyanosilylation of Ketones. J. Am. Chem. Soc., 122(30) 7412–7413.

Kanai, M., et al. (2000) Design of a new bifunctional asymmetric catalyst from carbohydrates: application to catalytic asymmetric cyanosilylation of aldehydes and acetophenone. Tetrahedron Letters, 41(14) 2405–2409.

*Primary Examiner*—Taofiq Solola
(74) *Attorney, Agent, or Firm*—Knobbe Martens Olson & Bear, LLP (57) ABSTRACT

A ligand expressed by a general formula (1) in claim 1, wherein $R^1$, $R^2$ and $R^3$ denote substituting groups on aromatic rings, X is P or As, and n is 1 to 3.

9 Claims, 1 Drawing Sheet

LIGANDS AND ASYMMETRIC CATALYSTS MADE BY USING THE SAME

This appln is a 371 of PCT/JP01/05323 filed Jun. 21, 2001.

DETAILED DESCRIPTION OF THE INVENTION

The present invention relates to ligands and asymmetric catalysts using such ligands. More particularly, the invention relates to asymmetric catalysts which promote cyanosilylation such a manner that an enantiomic reaction may be selectively effected.

PRIOR ART

The asymmetric catalyst means a catalyst that can itself produce an optically active substance and can discriminate enatiomers. Various products can be obtained simply by utilizing, as starting materials or the like, various products obtained with use of the asymmetric catalysts.

Investigations are now intensively being made on asymmetric catalysts for cyanation of carbonyl compounds such as aldehydes, imines, ketones, etc. With respect to an example of chemical catalysts used, a catalyst exhibiting an enantiomer excess of around 72% at the maximum for the arylmethyl ketones has been known.

However, no practical asymmetric catalyst has not been reported for the ketones. In actual, even the above-mentioned chemical catalysts used have a problem that they cannot be applied to ethylketone (30%) or an aliphatic ketone. If an asymmetric catalyst which can act upon general ketones including ethyl ketone and the aliphatic ketones can be obtained, large quantities of useful materials required in large amounts for medical and pharmaceutical researches, such as quaternary α-hydroxycarboxylic acid, quaternary β-amino alcohol, etc. can be simply synthesized. Therefore, development for the effectively catalytic cyanosilylation of ketones has been eagerly awaited for a long time. However, such asymmetric catalysts have not come into existence.

SUMMARY OF THE INVENTION

It is therefore an object of the present invention to provide asymmetric catalysts which can act upon widely general ketones.

In order to accomplish the above-mentioned object, the present inventors had repeatedly made fundamental studies of catalytic cyanosilylation, etc. of such as aldehydes and imines, and consequently the inventors discovered compounds according to the present invention. The ligand according to the present invention is expressed by the formula (8).

(8)

in which in which $R^1$, $R^2$ and $R^3$ denote substituting groups on aromatic rings, X is P or As, and n is 1 to 3.

The ligand according to the present invention is also expressed by the formula (9).

(9)

in which $R^1$, $R^2$ and $R^3$ denote substituting groups on aromatic rings, R is an electron-withdrawing group, X is P or As, and n is 1 to 3.

In the ligand according to the present invention, the above electron-withdrawing group is at least one selected from the group consisting of —$NH_3$, —$CF_3$, —$CCl_3$, —$NO_2$, —CN, —$CHO_4$, —$COCH_3$, —$COCH_3$, —$CO_2H$, —$SO_2CH_3$ and groups having the following formulae (10) to (13).

(10)

(11)

(12)

(13)

in which $R^5$ in the formula (10) is a substituting group on an aromatic ring.

The asymmetric catalyst according to the present invention is characterized in that a metal is bonded to a catechol moiety of the above ligand.

The asymmetric catalyst according to the present invention is characterized in that the metal is bonded to the catechol moiety in the form of a metallic complex.

The asymmetric catalyst is characterized in that the metallic complex has a structure expressed by a formula (14).

(14)

As a preferred embodiment of the asymmetric catalyst according to the present invention, the metal is at least one metal selected from the group consisting of titanium, zirconium, ytterbium, aluminum and gallium.

As another preferred embodiment of the asymmetric catalyst according to the present invention, the metal is a rare earth metal.

As a further preferred embodiment of the asymmetric catalyst according to the present invention, the rare earth metal is at least one metal selected from the group consisting of La, Ce, Pr, Nd, Pm, Sm, Eu, Gd, Dy, Ho and Er.

A method for producing a siloxy nitrile is characterized by reacting a ketone with a silyl cyanide in the presence of the above asymmetric catalyst.

As a preferred embodiment of the siloxy nitrile-producing method according to the present invention, the ketone is one selected from the group consisting of acetophenone, acetonaphthone, propiophenone, indanone, enones, cyclohexylmethyl ketone, n-alkanone and 2-heptanone.

As another preferred embodiment of the siloxy nitrile-producing method according to the present invention, the silylcyanide is at least one selected from the group consisting of trimethyl silylcyanide, triethyl silyl cyanide and t-butyldimethyl silyl cyanide.

As another preferred embodiment of the siloxy nitrile-producing method according to the present invention, the reaction is effected in the presence of a coordinating solvent.

As a further preferred embodiment of the siloxy nitrile-producing method according to the present invention, the coordinating solvent is selected from the group consisting of tetrahydrofuran (THF), dimethoxy ethane and ether.

Embodiments of the Present Invention

The ligand according to the present invention is expressed by the following formula.

(15)

in which $R^1$, $R^2$ and $R^3$ denote substituting groups on aromatic rings, X is P or As, and n is 1 to 3. n is not limited to an integer. Therefore, the catalyst can be obtained by using plural ligands with different n values.

The ligand according to the present invention is expressed by the following formula.

(16)

in which $R^1$, $R^2$ and $R^3$ denote substituting groups on aromatic rings, $R^4$ is an electron-withdrawing group, X is P or As, and n is 1 to 3. n is not limited to an integer. Therefore, the catalyst can be obtained by using plural ligands with different n values.

Figure 2:
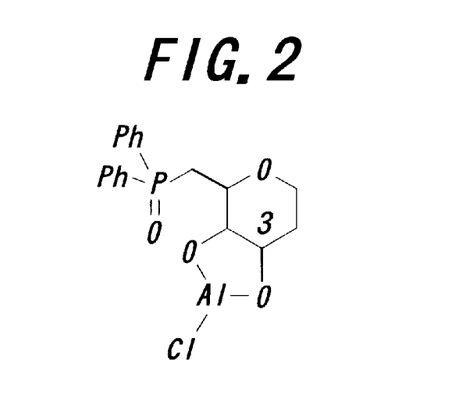
FIG. 2 is a figure showing a phosphine oxide catalyst.
Figure 3:
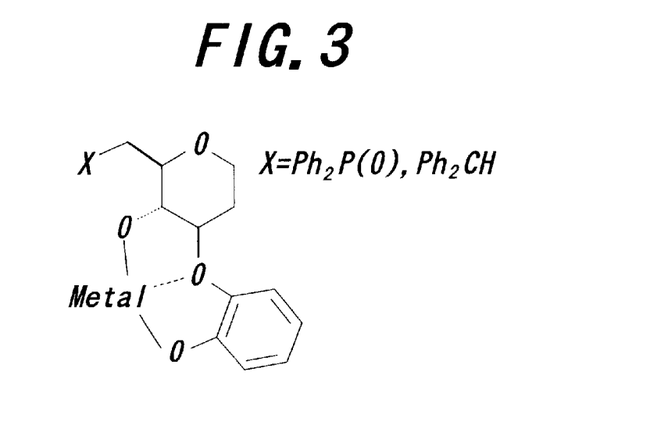
FIG. 3 is a figure showing a catalyst in which a catechol moiety is introduced at a C3 hydroxyl group of an alcohol.

During the course of their studies to develop novel asymmetric catalysts based on the concept of functional catalysts, the present inventors discovered that a Lewis acid (A1)-a Lewis base (phosphine oxide) catalyst (shown in FIG. 2) can promote cyanosilylation of acetophenone, but with low enantiomer excess (20%). To improve the enatioselectivity, the inventors planned to introduce a catechol moiety at the C3 hydroxyl group. The coordination of an ether oxide at the C3 makes it possible to form a complex as shown in FIG. 3, for example. As a result, the phenol group of the catechol must be fixed at an α-side (anti to the phosphorus, concave side) of the catalyst. In view of this, the inventors contrived to define the position of the coordinating ketone at the β-side, syn to the Lewis basic phosphine oxide. Therefore, the inventors designed the ligands expressed by the formulae (15) and (16).

For example, the ligand giving the skeleton in the formula (15) can be synthesized as follows. Reactions during the synthesis process are shown in the reaction scheme (17).

After an alcohol 1 is converted to a sodium alkoxide, a product 2 in which a catechol moiety is introduced into a hydroxyl group of the alcohol 1 by a nucleophilic substitution reaction for an allene-chronium complex is obtained. The alcohol as a starting material is not particularly limited, but an alcohol obtained from a sugar as a starting material may be recited, for example. After the acetal 2 is reduced to a product 3 with DIBAL-H, the alcohol is tosylated to a product 4. The product 4 is reacted with Ph₂PK, and the resulting phosphine is oxidized with H₂O₂, thereby obtaining a product 5. A benzyl group is removed from the product 5 with a palladium (Pd/C) catalyst through reduction, and then a product 1-L can be obtained by removing the protection of methyl ether with AlCl₃-EtSH.

In this way, the ligand 1-L can be readily synthesized in a scale of around 5 g from the known alcohol as shown in the reaction scheme 17.

In particular, a synthesis of a product in which R4 is a group given by a formula (3) is explained as follows. Reactions in a synthesis course are shown in a formula scheme 18.

Reaction conditions and reagents in the reaction scheme 18 are:
(a) 7, NaH, THF; 12, 84% (b) TBAF, THF, 99%; (c) PDC, MS4A, CH2Cl2, 94%; (d) PhMgBr, THF, 95%; (e) PDC, MS4A, CH₂Cl₂, 88%; (f) TsOH·MeOH, 97%; (g) TsCl, py, 83%; (h) ph₂PK(2.2 equiv.), THF; (i) H₂O₂, MeOH·H₂O, 40% (2 Steps); (j) LiI, DMF, 150° C., 80%.

After an alcohol 6 is converted to a sodium alkoxide, a product 8 in which a catechol moiety is introduced in a hydroxyl group of the alcohol 6 by a nucleophilic substitution reaction for an allene-chronium complex is obtained. The alcohol as a starting material is not particularly limited, but an alcohol obtained from a sugar as a starting material may be recited. After the TBS group is removed, a product 9 is synthesized by oxidation and addition of a Grignard reagent, and oxidation. The protection of the acetal 9 is removed with an acid, and the primary alcohol is selectively tosylated to a product 10. The product 10 is reacted with $Ph_2PK$, and the resulting phosphine is oxidized with $H_2O_2$. Then, a product 2-L can be obtained by removing the methyl group.

$R^1$, $R^2$, $R^3$ and $R^5$ are the substituting groups on the aromatic ring, and are not particularly limited. As the substituting groups, an alkyl, an ether, an amine, an ester, etc. may be specifically recited. From the standpoint of enhancing a Lewis acidity, the ester group is preferred as $R^1$. From the standpoint of enhancing the Lewis basicity, the ether group, the amine group and the alkyl group may be preferably recited as $R^2$ and $R^3$. From the standpoint of being three-dimensionally large, t-butyl group may be preferably recited as $R^5$.

The metal of the asymmetric catalyst according to the present invention is bonded to the catechol moiety of the ligand of the formula (1) or (2). The asymmetric catalyst is a catalyst that can itself form an optically active substance, and correctly means an enantiomer-discriminating catalyst. The metal can form a metal complex at the hydroxyl group of the catechol moiety of the ligand.

At least one kind of metals selected from the group consisting of titanium, zirconium, ytterbium, aluminum and gallium may be recited as the metal bonding to the catechol moiety. These metals may be used singly or in combination. Titanium may be recited as the metal from the standpoint of higher enatioselectivity.

Further, a rare earth metal may be recited as the metal bonding to the catechol moiety. For example, at least one kind of metals selected from the group consisting of La, Ce, Pr, Nd, Pm, Sm, Eu, Gd, Dy, Ho and Er may be recited as the rare earth metals. From the standpoint of obtaining the higher enantioselectivity, Gd and Sm may be preferably recited as the rear earth metals.

In the asymmetric catalyst according to the present invention, the metallic complex has the structure shown by the following formula.

(19)

Titanium, zirconium, etc. can take the formula (19). As $R^6$, an alkoxide, CN, Cl, F, Br, 1, etc. may be recited. The asymmetric catalyst can be stabilized with the ligand using these alkoxide, CN, Cl, F, Br, I or the like as the $R^6$. There are ytterbium, etc., which do not require a ligand of such as CN from their bonding configuration.

The asymmetric catalyst according to the present invention can catalyze the cyanosilylation of the ketones. The cyanosilylation means that a cyanide is nucleophilically added to a carbon of a carbonyl group, and the resulting alkoxide is supplemented with a silyl group.

According to the producing process of the present invention, the siloxynitrile can be obtained by reacting a ketone with a silylcyanide in the presence of the above asymmetric catalyst.

The siloxynitrile obtained by the cyanosilylation of the ketone enables the production of useful substances such as quaternary α-hydroxycarboxylic acids through a one step.

Here, the ketones to which the asymmetric catalyst according to the present invention is applicable are not particularly limited. Therefore, as the ketones in concern, general ketones including aliphatic ketones, aromatic ketones, etc. may be recited. For example, acetophenone, acetonaphthone, propiophenone, indanone, enones, cyclohexylmethyl ketone and n-alkanone may be recited. As the n-alkanone, 2-heptanone may be recited.

As the silylcyanide, trimethyl silylcyanide (TMSCN), triethyl silylcyanide, t-butyldimethyl silylcyanide, etc. may be recited. As the substance giving the silylnitrile in the same way, HCN, trimethyl tin cyanide, etc. may be recited besides silylcyanide.

Further, a solvent used in the cyanosilylation of the ketones is not particularly limited. As the solvent, for example, polarity-low solvents such as toluene and $CH_2Cl_2$, and coordinating solvents such as tetrahydrofuran (THF), dimethoxy ethane, ethers, etc. may be recited. From the standpoint of increasing the reaction speed and obtaining a higher enantioselectivity, the coordinating solvents such as tetrahydrofuran (THF), dimethoxy ethane, ethers, etc. may be recited as the solvent.

The reaction temperature of the cyanosilylation may be room temperature and not particularly limited, but −50° C. to room temperature, preferably −50~0° C., and more preferably −50~20° C. from the standpoint of obtaining the higher enantioselectivity. The reason why the lower limit is set at −50° C. is to enhance the enantioselectivity. The reason why the upper limit is set at room temperature is to raise the reaction speed.

The concentration of the ketones may be appropriately varied depending upon the products intended, and is not limited. The higher the concentration of the ketone, the higher the reaction speed tends to be.

EXAMPLES

Examples of the present invention will be explained, but the invention is not interpreted as being limited to the following ones. It is needless to say that the present invention may be appropriately varied without being deviating from the gist of the invention.

Example 1

After [3-benzyloxy-4-(2-methoxyphenyl)-tetrahydropyrano-[3, 2-d] [1, 3]dioxine-8-ol alcohol (hereinafter referred to as alcohol 1) is converted to a sodium alkoxide, a catechol moiety is introduced into a hydroxyl group of the alcohol by a nucleophilic substitution reaction for an allene-chromium complex, thereby obtaining 8-(2-methoxyphenyl)-2-phenyl-hexahydropyrano[3, 2-d] [1, 3]dioxine (hereinafter referred to as acetal 2). After acetal 2 is reduced to [3-benzyloxy-4-(2-methoxyphenyl)-tetrahydro-pyrane-2-yl]-methanol (hereinafter referred to as alcohol 3) with DIBAL-H, the alcohol 3 is tosylated to toluene-4-sulfonic acid 3-benzyloxy-4-(2-methoxyphenyl)-tetrahydro-pyrane-2-yl-methyl ester (hereinafter referred to as ester 4). The ester 4 is reacted with $Ph_2PK$, and the resulting phosphine is oxidized with $H_2O_2$, thereby obtaining 3-benzyloxy-2-(diphenylphosphinoylmethyl)-4-(2- methoxyphenyl)-tetrahydro-pyrane (hereinafter referred to pyrane 5). A benzyl group is removed from the pyrane 5 by reduction with a palladium catalyst (Pd/C catalyst), and the protection of the methyl ether is removed with AlCl$_3$-EtSH, thereby obtaining a ligand 1-L of the present invention.

The physical properties of the ligand thus obtained are shown below.

Melting point 219–200° C.

$^1$H NMR (500 MHz, CDCl$_3$) δ1.94(m, 1H), 2.14(m, 1H), 2.69(ddd, J=9.8, 15.0, 15.0 Hz, 1H), 2.84(ddd, J=2.8, 9.5, 15.3 Hz, 1H), 3.23(ddd, J=1.9, 12.2, 12.2 Hz, 1H), 3.34 (dddd, J=2.8, 7.0, 9.4, 9.8 Hz, 1H), 3.55(ddd, J=5.5, 8.9, 11.6 Hz, 1H), 3.73(dd, J=8.9, 9.4 Hz, 1H), 3.90(ddd, J=1.2, 5.7, 12.2 Hz, 1H), 6.71(ddd, J=1.9, 7.4, 7.4 Hz, 1H), 6.96(m, 3H), 7.51(m, 6H), 7.75(m, 4H), 8.92(s, 1H); $^{13}$C NMR (125 MHz, CDCl$_3$) δ31.62, 37.61(d, J=68 Hz), 65.50, 74.96, 76.11, 84.84, 117.22, 119.14, 122.45, 125.50, 128.90, 129.00, 129.03, 129.13, 130.60(d, J=10 Hz), 131.11(d, J=9 Hz), 132,47, 145.89, 150.15: $^{31}$P NMR(202 MHz, CDCl$_3$), δ34.0 IR 3422, 1156, 1103 cm$^{-1}$ C$_{25}$H$_{27}$O$_5$P (Analyzed): C, 67.67; H, 6.10%

(measured): C, 67.92; H, 5.94%

Example 2

Enantioselectivity was examined by using various metals. More specifically, different metals bonded to the ligand 1-L were examined with respect to catalyst for adding TMS (tetramethyl silane) into acetophenone. The reaction is shown in the following formula (20).

(20)

In Table 1 are shown results on the enatioselectivity of various metals.

TABLE 1

Influences of metals

| Metal | temperature/° C. | hours/h | yield/% | ee/% | R/S |
|---|---|---|---|---|---|
| Et$_2$AlCl | room temperature | 48 | 0 | — | — |
| Yb(O$^i$Pr)$_3$ | room temperature | 2 | 90 | 19 | S |
| Zr(O$^t$Bu)$_4$ | room temperature | 36 | 52 | 14 | R |
| Ti(O$^i$Pr)$_4$ | room temperature | 48 | 78 | 35 | R |
| Ti(O$^i$Pr)$_4$ | −20 | 36 | 44 | 73 | R |

In Table 1, "ee" denotes an enantiomeric excess. "R/S" denotes the absolute arrangement of the product. Although the Yb catalyst exhibited conspicuous activity, but the Ti catalysts the highest enantiomeric excess. Further, the reaction at −20° C. increased the enantiomeric excess up to 73%.

Example 3

Next, influences of solvents upon the asymmetric catalyst were examined. Results are shown in Table 2. The reaction is shown in the following formula (21).

(21)

It is interesting that both the reaction speed and the enantioselectivity increased in the case of coordinating solvents such as tetrahydrofuran (hereinafter referred to as THF) as compared with polarity-low solvents such as CH$_2$Cl$_2$ or toluene. It is also interesting that when the solvent was used in a higher concentration (3 M in the case of acetophenone), the reaction was more effectively carried out at −30° C. for 36 hours, thereby giving products in an amount of 92%cc at a yield of 85%. The best result was obtained when the reaction condition was that the ligand 1-L was contained in the case of 10 mol % of Ti(O$^i$Pr)$_4$ and the THF solvent.

TABLE 2

Influences of solvents

| Solvent | Concentration/M | temperature/° C. | hours/h | yield/% | ee/% |
|---|---|---|---|---|---|
| CH$_2$Cl$_2$ | 0.65 | −20 | 36 | 44 | 73 |
| toluene | 0.65 | −20 | 36 | 40 | 70 |
| THF | 0.65 | −20 | 36 | 58 | 83 |
| THF | 3 | −30 | 36 | 85 | 92 |

Example 4

The newly developed asymmetric catalysts exhibit a wide appreciation range as the high enantioselectivity for various ketones including the aromatic ketones and the aliphatic ketones. Results are shown in Table 3. The reaction is shown in the following formula (22).

(22)

More specifically, ketones having low reactivity, such as propiophenone 9f and iondanone 9e, gave products at yields of 89% and 72% and enantiomeric excesses of 91% and 69%, respectively. Enone 9g gave an adduct product with complete selectivity. Even simple n-alkanone 9j gave a product with an enantiomeric excess of 76%.

Further, 2-trimethylsiloxy-2-(2'-naphthyl)-propane nitrile (product 10d) could be converted to a quaternary hydroxyester or an aldehyde (DIBAL-H) (HCl-EtOH, at 90° C. for 3 hours) by a single step, without decreasing an enantiomeric excess.

TABLE 3

Catalytically asymmetric cyanosilylation of ketones

| No. | Ketone | | temperature/ °C. | hours/h | yield/% | ee/% |
|---|---|---|---|---|---|---|
| 1 | 4-R-C₆H₄-C(O)CH₃ | R = H 9a | −30 | 36 | 85 | 92 |
| 2 | | R = CH₃ 9b | −30 | 84 | 80 | 90 |
| 3 | | R = Cl 9c | −40 | 80 | 82 | 92 |
| 4 | 2-acetylnaphthalene | 9d | −40 | 80 | 82 | 96 |
| 5 | 1-indanone | 9e | −40 | 96 | 72 | 69 |
| 6 | propiophenone | 9f | −20 | 64 | 89 | 91 |
| 7 | (E)-4-phenyl-3-buten-2-one | 9g | −50 | 86 | 72 | 91 |
| 8 | acetophenone | 9h | −50 | 36 | 86 | 90 |
| 9 | 4-phenyl-2-butanone | 9I | −50 | 36 | 92 | 88 |
| 10 | 2-heptanone | 9j | −50 | 36 | 88 | 76 |

Example 5

In order to confirm the structure of the asymmetric catalyst, NMR analysis was carried out. When a mixture of Ti(O'Pr)4 and the product 1-L was heated in toluene at 75° C. for 1 hour, the production of 2 equivalents of $^i$PrOH was observed with $^1$HNHR. Therefore, a precatalyst in this stage contains titanium isopropoxide (1: Mtl=Ti(O$^i$Pr)$_2$). After toluene was evaporated, THF and TMSCN (2 equivalents for Ti) were added. Then, peaks corresponding to TMSO$^i$Pr appeared, which revealed the production of titanium cyanide. It is considered that about 70% of titanium contains monocyanide after one hour at room temperature. This is anticipated from the remaining TMSCN (0.44 ppm) and an accumulating percentage of TMSOPR produced. Further addition of acetophenone (10 equivalents for Ti) and TMSCN (15 equivalents for Ti) starts the reaction, which almost completely changes Ti to monocyanide. Therefore, the asymmetric catalyst can be present as a complex of titanium monocyano monoisoproxide (1: Mt1=Ti(CN)(O$^i$Pr). As mentioned later, the complex of the titanium monocyanide is formed by using 1 equivalent of TMSCN for a longer reaction time period (10 hours).

In order to obtain further knowledge of the characteristics of this reaction, a reaction order for the catalyst was determined through chemically kinetic studies.

Further, it was considered based on labelling tests using TMS$^{13}$CN that the cyanide was obtained through a reaction from not titanium cyanide but TMSCN. That is, an active titanium catalyst containing $^{12}$CN was prepared (at room temperature for 10 hours) from Ti(O$^i$Pr)$_4$, 1-L (1 equivalent) and TMS $^{12}$CN (1 equivalent). After the complete consumption of TMS$^{12}$CN was confirmed with $^1$HNMR, 9a (1 equivalent) and TMS 3CN (1 equivalent) were added. It was confirmed with $^{13}$C NMR that 77% of $^{13}$CN was taken into the product 10a. These results suggest that the titanium cyanide functions not as a CN source but as a Lewis acid only.

Figure 1:
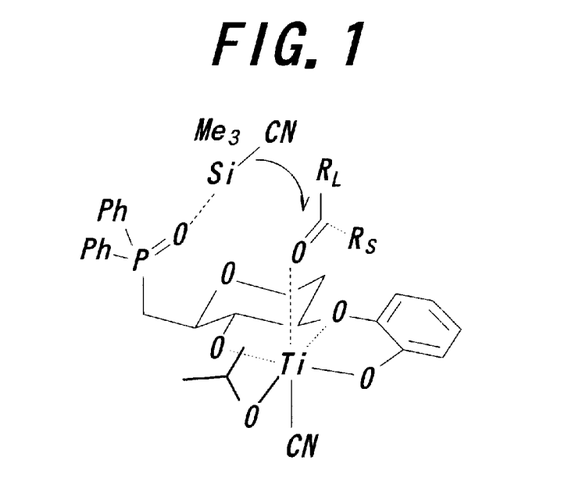
FIG. 1 is a figure showing an example of a catalytic action of an asymmetric catalyst according to the present invention containing a metal and phosphine oxide.

In order to clarify the role of the phosphine oxide in the enantioselectivity, a catalyst having a diphenyl methyl group instead of the phosphine oxide was used. As a result, the reaction very slowly proceeded at room temperature with respect to the catalyst having the diphenylmethyl group, and 2-trimethylsiloxy-2-phenylpropanitrile (10a in the formula (22)) and 2-trimethylsiloxy-2-methyl-4-phenylbutane nitrile (10i of the formula (22)) were obtained at yields 31% and 33% (80 hours), respectively, both with an enantiomeric excess of 2%. From this point of view and our previous investigation results, it is seen that titanium and oxygen atoms in the phosphine oxide form a double active mechanism of the catalyst, which mechanism activates the ketones and TMSCN as the Lewis acid and the Lewis base, respectively (FIG. 1).

Example 6

After [3-benzyloxy-4-(2-methoxyphenyl)-tetrahydropyrano-[3, 2-d] [1, 3]dioxine-8-ol alcohol (hereinafter referred to as alcohol 1) is converted to a sodium alkoxide, a catechol moiety is introduced into a hydroxide group of the alcohol by a nucleophilic substitution reaction for an allene-chromium complex, thereby obtaining di-t-butyl-[4-methoxy-3-(2-phenyl-hexahydropyrano[3,2-d] [1, 3]dioxine-8-yloxy)-benzyoxy]-methyl-silane. After TBS was removed, [4-methoxy-3-(2-phenyl-hexahydropyrano[3, 2-d] [1,3]dioxine-8-yloxy)-phenyl]phenyl methanone (corresponding to 9 in the formula (18)) was obtained by oxidation, addition of a phenyl Grignard reagent and oxidation. The acetal of 9 was removed, and the primary alcohol was selectively tosylated, thereby obtaining toluene sulfonate 4-(5-benzoyl-2-methoxy-phenoxy-3-hydroxy-tetrahydro-pyrane-2-ylmethyl ester (corresponding to 10). The product 10 is reacted with Ph$_2$PK, the resulting phosphine was oxidized with H$_2$O$_2$, and the methyl ether was removed, thereby obtaining the ligand 2-L.

The physical properties of the ligand 2 according to the present invention are shown below.

H-NMR (500 MHz, CDCl$_3$); δ1.94(m, 1H), 2.16(m, 1H), 2.72(ddd, J=9.45, 15.0, 15.0 Hz, 1H), 2.84(ddd, J=3.35, 9.45, 15.3 Hz, 1H), 3.23(m, 1H), 3.38(ddd, J=3.05, 9.15, 16.5 Hz, 1H), 3.60(ddd, J=5.20, 8.90, 11.3 Hz, 1H), 3.74(dd, J=8.90, 9.20 Hz, 1H), 3.89(m, 1H), 6.98 (d, J=8.25 Hz, 1H), 7.43–7.80(m, 18H), 9.73(s, 1H):

$^{13}$C—NMR (125.65 MHz, CDCl$_3$); δ31.5, 36.0 (d, J=68.2 Hz), 65.3, 74.7, 75.8, 84.8, 116.5, 123.8, 128.0, 128.7, 128.8, 128.8, 128.9, 129.0, 129.0, 129.6, 130.0, 130.5, 130.6, 130.8, 130.9, 131.0, 131.2, 131.7, 132.1, 132.3, 138.3, 145.7, 154.8, 195.1:

31P-NMR (202.35 MHz, CDCl$_3$); δ34.5 optical rotation degree: $[\alpha]_D^{27}$+13(c=2.34, CHCl$_3$)

Example 7

Enantioselectivity was examined by using titanium and a benzoyl group as a metal and R4, respectively. A reaction formula is shown below.

(23)

Results on the enantioselectivity are shown in Table 4.

TABLE 4

| Metal | R$^7$ | temperature/° C. | hours/h | yield/% | ee/% | R/S |
|---|---|---|---|---|---|---|
| Ti | phenyl | −30° C. | 44 | 76% | 97% | R |
| Ti | N-C$_5$H$_{11}$ | −50° C. | 44 | 71% | 86% | S |

In Table 4, "ee" denotes an enantiomeric excess. "R/S" denotes the absolute arrangement of the product. When the phenyl group and n-C$_5$H$_{11}$ were used as R$^7$, they exhibited high enantioselectivity values of 97% and 86%, respectively.

Example 8

Next, enantioselectivity was examined with respect to R$^4$ in the formula (2) being the phenyl group, the n-C$_5$H$_{11}$ or that of the formulae (4), (5) and (6). Results are shown in Table 5.

TABLE 5

| Metal | R$^7$ | temperature/° C. | hours/h | yield/% | ee/% | R/S |
|---|---|---|---|---|---|---|
| Ti | phenyl | −30° C. | 44 | 76% | 97% | R |
| Ti | N-C$_5$H$_{11}$ | −50° C. | 44 | 71% | 86% | R |

Each of the cases where R$^4$ is the phenyl group, the n-C$_5$H$_{11}$, or the groups in the formula (4), (5) or (6) exhibited high enantioselectivity.

Example 9

Enantioselectivity of novel asymmetric catalysts was examined with use of various ketones. Results are shown in Table 6.

TABLE 6

| No. | Ketone | | temperature/°C | hours/h | yield/% | ee/% |
|---|---|---|---|---|---|---|
| 1 | 4-R-C₆H₄-C(O)-CH₃ | R = H | −20 | 88 | 92 | 94 |
| 2 | | R = Cl | −25 | 92 | 72 | 90 |
| 3 | phenyl propyl ketone | | −10 | 92 | 90 | 92 |
| 4 | cyclohexyl methyl ketone | | −30 | 70 | 91 | 93 |
| 5 | (E)-oct-3-en-2-one | | −30 | 92 | 72 | 90 |
| 6 | heptan-2-one | | −45 | 92 | 80 | 82 |

As a result, each of them exhibited a high enantiomeric excess.

Example 10

Next, enantioselectivity of novel asymmetric catalysts was examined with use of various rare earth metals as metals. A reaction formula is shown below. Results on the enantioselectivity are shown in Table 7.

TABLE 7

| Metal | Metal:ligand (1-L)(molar ratio) | $R^7$ | temperature/°C | hours/h | yield/% | ee/% | R/S |
|---|---|---|---|---|---|---|---|
| Gd | 1:2 | phenyl | −40 | 1 | 98 | 92 | S |
| Pr | 1:2 | phenyl | −40 | 1.5 | 98 | 77 | S |
| Yb | 1:1 | phenyl | −40 | 2 | 90 | 18 | S |
| La | 1:1 | phenyl | −40 | 4.5 | 91 | 53 | S |
| Nd | 1:1 | phenyl | −40 | 2 | 99 | 67 | S |

In Table 7, "ee" denotes an enantiomeric excess of the enantiomers. "R/S" denotes the absolute arrangement of the product. Tests were effected with use of the asymmetric catalysts at molar ratios of the metal: the ligand as shown in Table 7.

As a result, when the phenyl group, the PhCHCH group, and the M-$C_5H_{11}$, a high enantiomeric excess was exhibited.

Example 11

Various ketones were subjected to cyanosilylation by using asymmetric catalysts according to the present invention. Results are shown in Table 8.

TABLE 8

| No. | Ketone | temperature/ °C. | hours/h | yield/% | ee/% |
|---|---|---|---|---|---|
| 1 | phenyl propyl ketone | −60 | 4 | 74 | 97 |
| 2 | cinnamyl methyl ketone | −60 | 14 | 97 | 80 |
| 3 | acetophenone | −40 | 1.5 | 92 | 92 |
| 4 | 2-hexanone | −60 | 2 | 90 | 46 |

In Table 8, "ee" denotes an enantiomeric excess. The ketones were subjected to the cyanosilylation with using an asymmetric catalyst constituted by 5 mol % of Gd(O'Pr) and 10 ml % of the ligand 1-L. THF was used as a solvent.

As is clear from Table 8, an excellent enantiomeric excess was exhibited in each case.

Effect of the Invention

The ligand according to the present invention exhibits the advantageous effect that it can be used as a ligand of the asymmetric catalyst.

Further, the asymmetric catalyst according to the present invention can realize the selective cyanosilylation of the ketone at a high enantioselectivity. The product (chiral cyanohydrins) can be effectively converted to the asymmetric quaternary α-hydrocarbonyl derivative and β-amino alcohol. This affords a novel synthetic method for the main construction of the asymmetric tertiary hydroxycarbonyl derivative. Thus, the present invention can make it more readily to effective construction of the to the asymmetric

What is claimed is:

1. A ligand expressed by a general formula (1):

in which $R^1$, $R^2$ and $R^3$ are selected from alkyl, ether, amine and ester, X is P or As, and n is 1 to 3.

2. Ligand expressed by a general formula (2):

in which $R^1$, $R^2$ and $R^3$ are selected from alkyl, ether, amine and ester, $R^4$ is an electron-withdrawing group, X is P or As, and n is 1 to 3.

3. The ligand set forth in claim 2, wherein the electron-withdrawing group is at least one selected from the group consisting of —$NH_3$, —$CF_3$, —$CCL_3$, —$NO_2$, —CN, —$CHO_4$, —$COCH_3$, —$COCH_3$, —$CO_2H$, —$SO_2CH_3$ and groups having the following formulae (3) to (6):

in which $R^5$ in the formula (3) is a substituting group on an aromatic ring.

4. An asymmetric catalyst in which a metal is bonded to a catechol moiety of the ligand in claim 1 or claim 2.

5. The asymmetric catalyst set forth in claim 4, wherein the metal is bonded to the catechol moiety in the form of a metallic complex.

6. The asymmetric catalyst set forth in claim 5, wherein the metallic complex has a structure expressed by a formula (7):

in which M is the metal, and $R^6$ is absent, an alkoxide, CN, Cl, F, Br or I.

7. The asymmetric catalyst set forth in claim 4 wherein the metal is at least one metal selected from the group consisting of titanium, zirconium, ytterbium, aluminum and gallium.

8. The asymmetric catalyst set forth in claim 4 wherein the metal is a rare earth metal.

9. The asymmetric catalyst set forth in claim 8, wherein the rare earth metal is at least one metal selected from the group consisting of La, Ce, Pr, Nd, Pm, Sm, Eu, Gd, Dy, Ho and Er.

* * * * *